(12) United States Patent
Ogata et al.

(10) Patent No.: US 12,232,880 B2
(45) Date of Patent: Feb. 25, 2025

(54) DATA PROCESSING APPARATUS, DATA PROCESSING METHOD, AND STORAGE MEDIUM STORING PROGRAM

(71) Applicant: Melody International Ltd., Kagawa (JP)

(72) Inventors: Yhuko Ogata, Kagawa (JP); Takayoshi Kunikata, Kagawa (JP); Takuya Sugimura, Kagawa (JP); Kazuhiro Hara, Kagawa (JP)

(73) Assignee: Melody International Ltd., Kagawa (JP)

( * ) Notice: Subject to any disclaimer, the term of this patent is extended or adjusted under 35 U.S.C. 154(b) by 401 days.

(21) Appl. No.: 17/536,098

(22) Filed: Nov. 29, 2021

(65) Prior Publication Data

US 2022/0079498 A1 Mar. 17, 2022

Related U.S. Application Data

(63) Continuation of application No. PCT/JP2021/011665, filed on Mar. 22, 2021.

(30) Foreign Application Priority Data

Apr. 22, 2020 (JP) .................................. 2020-076271

(51) Int. Cl.
*A61B 5/361* (2021.01)
*A61B 5/00* (2006.01)
(Continued)

(52) U.S. Cl.
CPC .......... *A61B 5/361* (2021.01); *A61B 5/02405* (2013.01); *A61B 5/1102* (2013.01);
(Continued)

(58) Field of Classification Search
CPC ... A61B 5/361; A61B 5/02405; A61B 5/1102; A61B 5/7246; A61B 5/7267;
(Continued)

(56) References Cited

U.S. PATENT DOCUMENTS

2011/0172729 A1   7/2011   Sweeney et al.
2015/0065894 A1*  3/2015   Airaksinen .......... A61B 5/7282
                                                   702/19

(Continued)

FOREIGN PATENT DOCUMENTS

JP   S63277034 A     11/1988
JP   2015517842 A     6/2015
JP   2019201886 A    11/2019

*Primary Examiner* — Catherine M Voorhees
(74) *Attorney, Agent, or Firm* — HAUPTMAN HAM, LLP

(57) ABSTRACT

A data processing apparatus includes: a data acquisition unit that acquires waveform data corresponding to biological information correlated with a heart rate and generates, on the basis of the acquired waveform data, a plurality of pieces of time series data whose starting timings are different from each other; a correlation value calculation unit that calculates an autocorrelation value of the plurality of pieces of time series data for each of a plurality of lags; and an image generation unit that generates the autocorrelation image data in which the autocorrelation values are indicated for each of coordinates corresponding to a plurality of combinations of a timing and a lag by mapping pixel values corresponding to autocorrelation values corresponding to the combinations of the timing and the lag to a coordinate plane, in which the timing is assigned to a first axis and the lag is assigned to a second axis.

8 Claims, 8 Drawing Sheets

(51) Int. Cl.
*A61B 5/024* (2006.01)
*A61B 5/11* (2006.01)

(52) U.S. Cl.
CPC .......... *A61B 5/7246* (2013.01); *A61B 5/7267* (2013.01); *A61B 5/7289* (2013.01)

(58) Field of Classification Search
CPC ... A61B 5/7289; A61B 5/743; A61B 5/02438; A61B 5/339; A61B 5/0245
See application file for complete search history.

(56) References Cited

U.S. PATENT DOCUMENTS

2015/0126875 A1* 5/2015 Poh ...................... A61B 5/7275
 600/479
2020/0375490 A1* 12/2020 Herrmann .............. A61B 5/363

\* cited by examiner

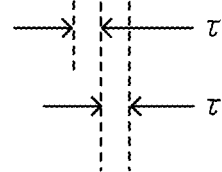

DATA PROCESSING APPARATUS, DATA PROCESSING METHOD, AND STORAGE MEDIUM STORING PROGRAM

CROSS-REFERENCE TO RELATED APPLICATIONS

The present application is a continuation application of International Application number PCT/JP2021/011665, filed on Mar. 22, 2021, which claims priority under 35 U.S.C § 119(a) to Japanese Patent Application No. 2020-076271, filed on Apr. 22, 2020. The contents of these applications are incorporated herein by reference in their entirety.

BACKGROUND

The present disclosure relates to a data processing apparatus, a data processing method, and a storage medium storing a program for facilitating detection of atrial fibrillation.

A technique for detecting atrial fibrillation on the basis of pulse waves is known (see, for example, Japanese Unexamined Patent Application Publication No. 2019-201886).

In the conventional technique, an occurrence of arrhythmia or atrial fibrillation is detected on the basis of the number of abnormal pulse waves detected within a predetermined measurement period. However, since there are abnormalities that cannot be detected by the number of pulse waves, it is necessary to improve accuracy of detecting an abnormality in heartbeat waves, pulse waves, or the like.

SUMMARY

The present disclosure focuses on this point and its object is to improve detection accuracy of an abnormality in heartbeat waves, pulse waves, or the like.

A data processing apparatus according to a first aspect of the present disclosure includes: a data acquisition unit that acquires waveform data corresponding to biological information correlated with a heart rate and generates, on the basis of the acquired waveform data, a plurality of pieces of time series data whose starting timings are different from each other; a correlation value calculation unit that calculates an autocorrelation value of the plurality of pieces of time series data for each of a plurality of lags; an image generation unit that generates the autocorrelation image data in which the autocorrelation values are indicated for each of coordinates corresponding to a plurality of combinations of a timing and a lag by mapping pixel values corresponding to autocorrelation values corresponding to the combinations of the timing and the lag to a coordinate plane, in which the timing is assigned to a first axis and the lag is assigned to a second axis; and an image output unit that outputs the autocorrelation image data.

A data processing method according to a second aspect of the present disclosure that is executed by a compute includes: acquiring waveform data corresponding to biological information correlated with a heart rate; generating a plurality of pieces of time series data whose starting timings are different from each other; calculating an autocorrelation value of the plurality of pieces of time series data for each of a plurality of lags; generating the autocorrelation image data in which the autocorrelation values are indicated for each of coordinates corresponding to a plurality of combinations of a timing and a lag by mapping pixel values corresponding to a plurality of autocorrelation values corresponding to the combinations of the timing and the lag to a coordinate plane, in which the timing is assigned to a first axis and the lag is assigned to a second axis; and outputting the autocorrelation image data.

A storage medium storing a program according to a third aspect of the present disclosure is a medium that non-transitory stores a program that causes a computer to function as: a data acquisition unit that acquires waveform data corresponding to biological information correlated with a heart rate and generates, on the basis of the waveform data, a plurality of pieces of time series data whose starting timings are different from each other; a correlation value calculation unit that calculates an autocorrelation value of the plurality of pieces of time series data for each of a plurality of lags; an image generation unit that generates the autocorrelation image data in which the autocorrelation values are indicated for each of coordinates corresponding to a plurality of combinations of a timing and a lag by mapping pixel values corresponding to a plurality of autocorrelation values corresponding to the combinations of the timing and the lag to a coordinate plane, in which the timing is assigned to a first axis and the lag is assigned to a second axis; and an image output unit that outputs the autocorrelation image data.

DETAILED DESCRIPTION

Hereinafter, the present disclosure will be described through exemplary embodiments, but the following exemplary embodiments do not limit the disclosure according to the claims, and not all of the combinations of features described in the exemplary embodiments are necessarily essential to the solution means of the disclosure.

Outline of a Data Processing System S

Figure 1:
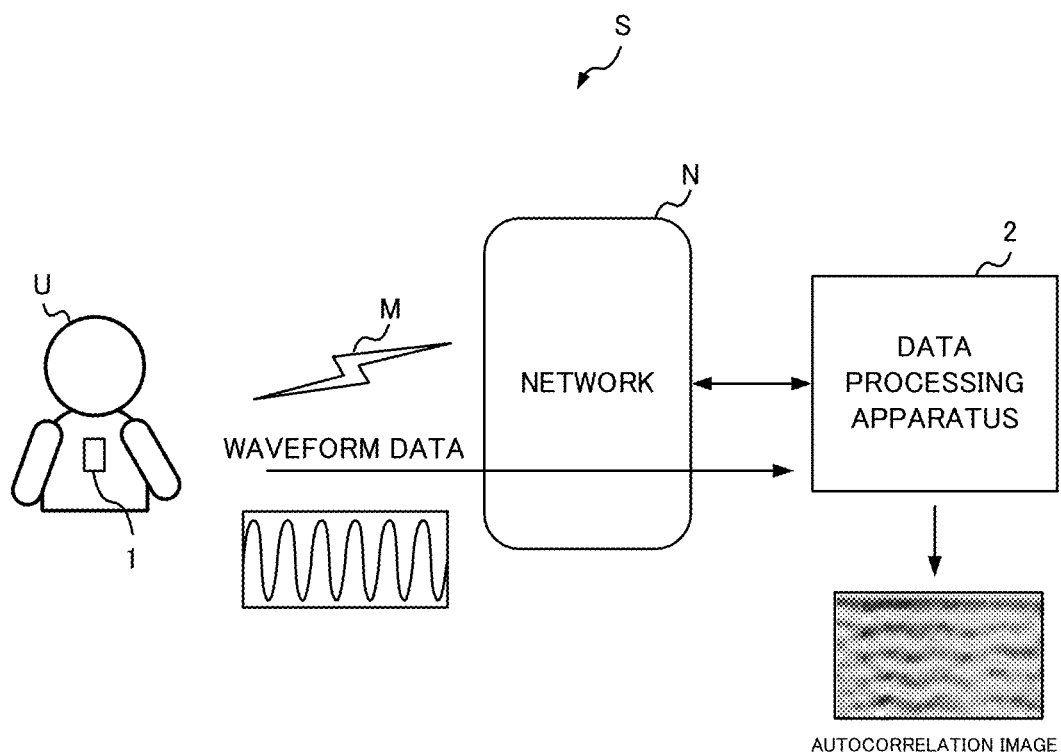
FIG. 1 shows an outline of a data processing system.

FIG. 1 shows an outline of a data processing system S. The data processing system S is a system for determining whether or not there is an abnormality in heartbeat waves, pulse waves, or the like by analyzing waveform data corresponding to biological information correlated with a heart rate such as heartbeat waves, pulse waves, or the like (hereinafter referred to as "heartbeat waves or the like") of the subject U.

The data processing system S includes a heart rate meter 1 and a data processing apparatus 2. The heart rate meter 1 and the data processing apparatus 2 can transmit and receive data via a network N. The network N includes Wi-Fi (a registered trademark), a mobile telephone network, or the Internet, for example.

The heart rate meter 1 is an example of a biological information measuring device that generates waveform data indicating the subject U's heartbeat waves or the like and transmits the generated waveform data to the data processing apparatus 2 via a wireless channel M and the network N. The heart rate meter 1 is not limited to a so-called heart rate meter, and may be a pulse wave meter or an electrocardiograph, for example. By being attached to a body part of the subject U such as his/her arm or chest, where the heartbeat waves or the like can be measured, the heart rate meter 1 can generate waveform data of the heart rate over 24 hours, for example.

The waveform data may be analog data or digital data. For example, the heart rate meter 1 samples an analog signal output from a sensor for measuring the heartbeat waves or the like every predetermined sampling time period (e.g., 30 milliseconds), and converts the sampled data into a digital value to generate digital data.

The data processing apparatus 2 is an apparatus for determining whether or not arrhythmia or atrial fibrillation is occurring in the subject U on the basis of the waveform data received from the heart rate meter 1, and is a computer, for example. The data processing apparatus 2 calculates an autocorrelation value of the waveform data and analyzes the calculated autocorrelation value to determine whether or not arrhythmia or atrial fibrillation is occurring in the subject U.

Specifically, the data processing apparatus 2 generates a plurality of pieces of time series data by extracting a portion of data corresponding to a predetermined time period (corresponding to a window width, which will be described later) from the waveform data. The data processing apparatus 2 calculates a plurality of autocorrelation values corresponding to a plurality of lags for each of the generated plurality of pieces of time series data. The data processing apparatus 2 can generate autocorrelation image data in which the timing, the lag, and the autocorrelation value are associated with each other, and identify that arrhythmia or atrial fibrillation is occurring on the basis of characteristics of an image that appears in the generated autocorrelation image data. Details will be described later. It should be noted that the lag is a time difference used when calculating the autocorrelation value in the time series data.

Configuration of the Data Processing Apparatus 2

Figure 2:
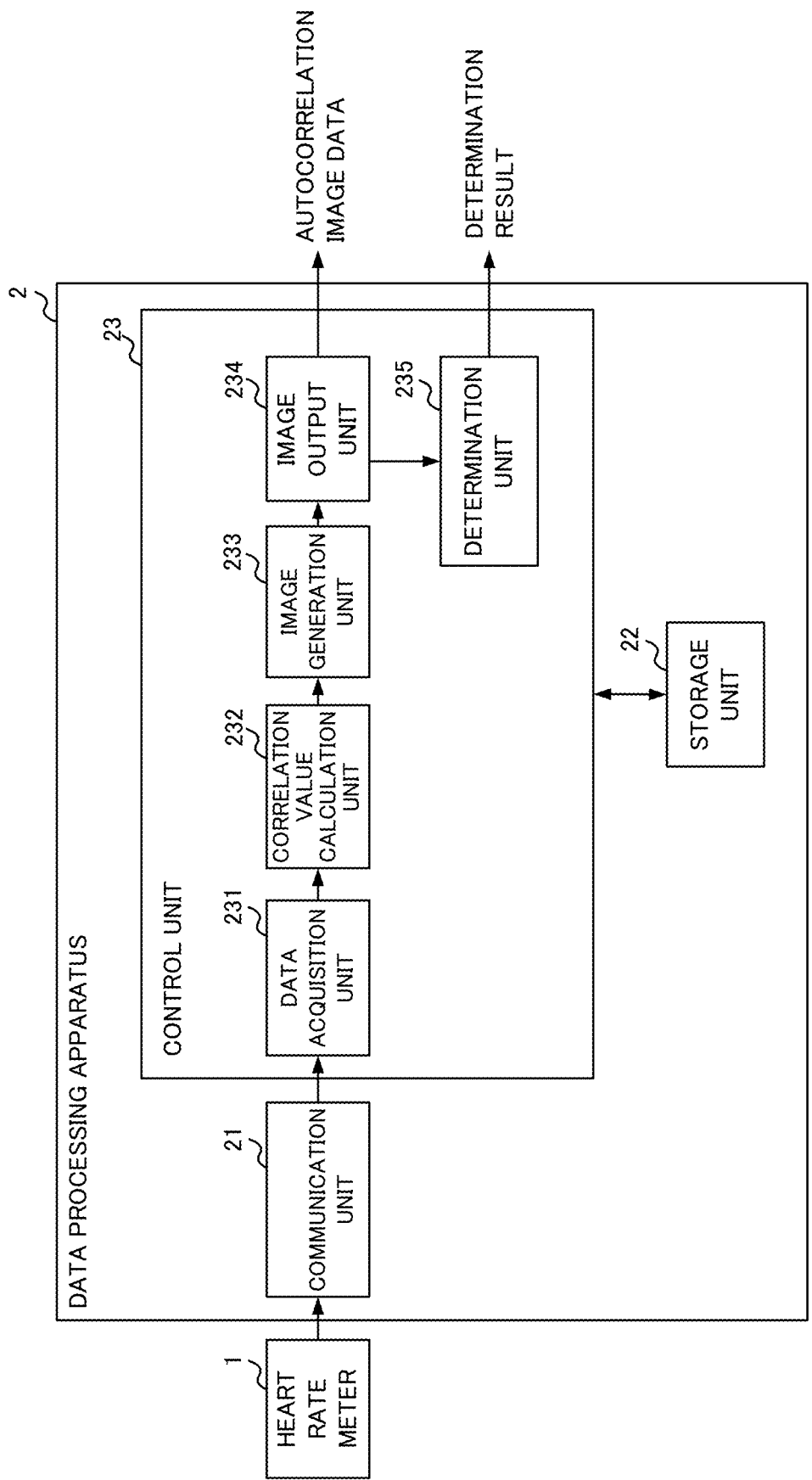
FIG. 2 shows a configuration of a data processing apparatus.

FIG. 2 shows a configuration of the data processing apparatus 2. The data processing apparatus 2 includes a communication unit 21, a storage unit 22, and a control unit 23. The control unit 23 includes a data acquisition unit 231, a correlation value calculation unit 232, an image generation unit 233, an image output unit 234, and a determination unit 235.

The communication unit 21 is a communication interface for receiving the waveform data from the heart rate meter 1 via the network N, for example. The communication unit 21 inputs the received waveform data to the data acquisition unit 231. The communication unit 21 may store the received waveform data in the storage unit 22.

The storage unit 22 includes a storage medium such as a read only memory (ROM), a random access memory (RAM), a hard disk drive (HDD), and the like. The storage unit 22 temporarily stores the waveform data received by the communication unit 21, for example. The storage unit 22 stores a program executed by the control unit 23.

The control unit 23 includes a central processing unit (CPU), for example. The control unit 23 functions as a data acquisition unit 231, a correlation value calculation unit 232, an image generation unit 233, an image output unit 234, and a determination unit 235 by executing the program stored in the storage unit 22.

The data acquisition unit 231 acquires, via the communication unit 21, the waveform data corresponding to the heartbeat waves or the like transmitted by the heart rate meter 1, and stores the waveform data in a buffer area (for example, an area in which 1024 pieces of data are stored) first and then outputs the waveform data to the correlation value calculation unit 232, for example. The data acquisition unit 231 may perform filtering on the waveform data to remove high-frequency components included therein first and then output the waveform data to the correlation value calculation unit 232. The data acquisition unit 231 may acquire the waveform data from the heart rate meter 1 in real time, or may acquire the waveform data periodically (for example, every 24 hours). Also, the data acquisition unit 231 may acquire waveform data to be analyzed at the time of analyzing the waveform data.

The data acquisition unit 231 generates, on the basis of the acquired waveform data, a plurality of pieces of time series data whose starting timings are different from each other. The time series data is data obtained by cutting out data corresponding to a predetermined window width from the waveform data, for example. The predetermined window width is a time width longer than the minimum time required to identify the trend of arrhythmia or atrial fibrillation, and is, for example, a time width longer than a time period for two cycles of waveform data. The data acquisition unit 231 selects a plurality of windows with the predetermined window width whose starting timings are different from each other by the sampling time, and generates a plurality of pieces of time series data by cutting out data from the waveform data with the selected plurality of windows. The data acquisition unit 231 inputs the generated plurality of pieces of time series data to the correlation value calculation unit 232.

Figure 3A:
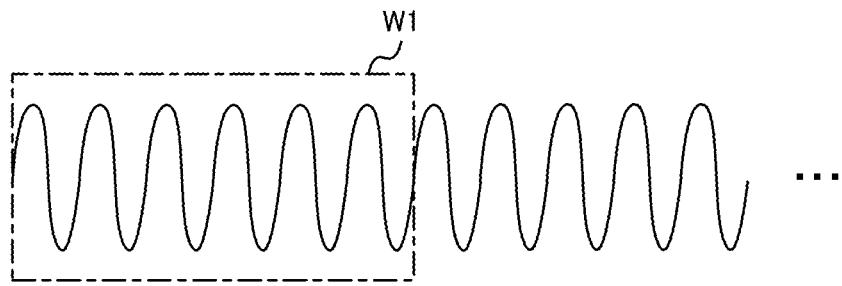
FIGS. 3A, 3B, 3C, and 3D each illustrate time series data.
Figure 3B:
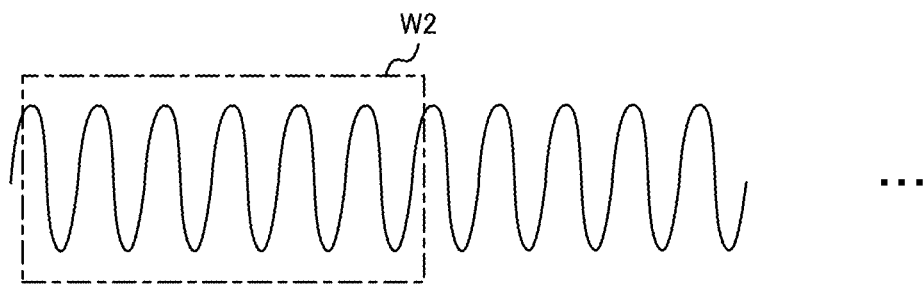
Figure 3C:
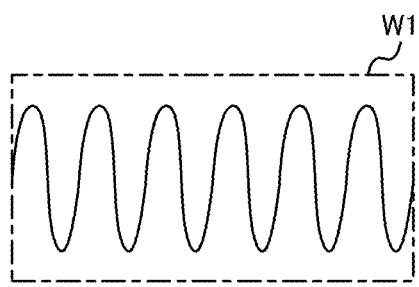
Figure 3D:
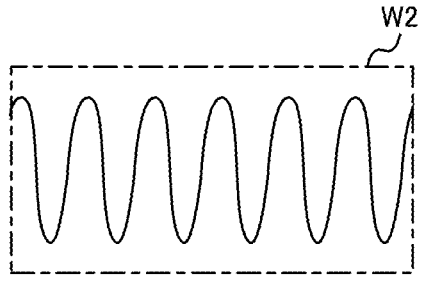

FIGS. 3A, 3B, 3C, and 3D each illustrate time series data. FIGS. 3A and 3B each show the waveform data acquired by the data acquisition unit 231, and the dashed-dotted lines show a window W1 and a window W2 whose starting timings are different from each other. FIG. 3C shows time series data generated by the data acquisition unit 231 by cutting out waveform data included in the window W1. FIG. 3D shows time series data generated by the data acquisition unit 231 by cutting out waveform data included in the window W2. The data acquisition unit 231 inputs the plurality of pieces of time series data generated in this manner to the correlation value calculation unit 232.

The data acquisition unit 231 may slice the waveform data with a line parallel to the time axis and convert data values that are greater than a value corresponding to this line into the value corresponding to the line. Because the data acquisition unit 231 operates in this manner, influences of noise can be removed.

The correlation value calculation unit 232 calculates autocorrelation values of the plurality of pieces of time series data for each of the plurality of lags. The correlation value calculation unit 232 calculates the autocorrelation values for each of the lags with $\tau$, $2\tau$, $3\tau$, ..., $n\tau$, which are integer multiples of a time interval $\tau$ between the closest plurality of pieces of data included in the time series data, as the plurality of lags, for example. For example, $\tau$ is an integer multiple of a sampling interval (for example, 30 milliseconds) of the waveform data. The "n" is an integer smaller than the number of pieces of data included in the time series data. The "n" is a value whereby a time, during which (i) the time series data and (ii) the time series data after having been time-shifted by nτ overlap with each other, is longer than the cycle of the heartbeat waves or the like. The "n" is a value equal to or less than half the number of pieces of data included in the time series data, for example.

Figure 4A:
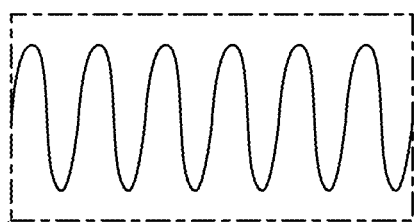
FIGS. 4A, 4B, and 4C each illustrate a process of a correlation value calculation unit calculating an autocorrelation value.
Figure 4B:
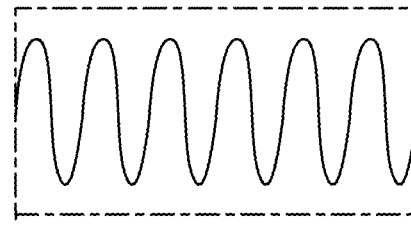
Figure 4C:
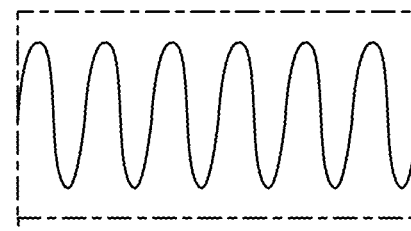

FIGS. 4A, 4B, and 4C each illustrate a process of the correlation value calculation unit 232 calculating the autocorrelation value. FIG. 4A shows first time series data shown in FIG. 3C, and FIG. 4B shows second time series data obtained by delaying the time series data shown in FIG. 4A by a lag τ. FIG. 4C shows third time series data obtained by delaying the first time series data shown in FIG. 4A by a lag 2τ. The correlation value calculation unit 232 calculates an autocorrelation value corresponding to the lag τ by calculating a cross-correlation value between the first time series data shown in FIG. 4A and the second time series data shown in FIG. 4B. Similarly, the correlation value calculation unit 232 calculates an autocorrelation value corresponding to the lag 2τ by calculating a cross-correlation value between the first time series data and the third time series data shown in FIG. 4C.

When there is no abnormality in the heartbeat waves or the like, approximately the same shaped waveforms repeat periodically in the heartbeat waves or the like. Therefore, when there is no abnormality in the heartbeat waves or the like, the autocorrelation value calculated by the correlation value calculation unit 232 becomes the largest at a lag that matches the integer multiple of the cycle of the heartbeat waves or the like. On the other hand, when there is an abnormality in the heartbeat waves or the like, the cycle of the heartbeat waves or the like is disrupted, or an irregular peak exists between peaks of the heartbeat waves or the like. As a result, the autocorrelation value does not become the largest at the lag that matches the integer multiple of the cycle of the heartbeat waves or the like, or a difference value between the maximum value and the minimum value of the autocorrelation value becomes smaller than the difference value occurring in normal cases. The correlation value calculation unit 232 inputs the calculated autocorrelation value to the image generation unit 233 so that it can be determined whether or not there is an abnormality in the heartbeat waves or the like using such characteristics of the autocorrelation value.

The correlation value calculation unit 232 may input an autocorrelation value after normalization to the image generation unit 233. The correlation value calculation unit 232 performs normalization such that the maximum autocorrelation value becomes 1 by dividing the calculated autocorrelation value by the autocorrelation value when the lag is zero, for example. The correlation value calculation unit 232 may normalize an autocorrelation value by dividing the autocorrelation value by a mean value of the autocorrelation values in the plurality of pieces of time series data corresponding to the plurality of timings. Because the correlation value calculation unit 232 normalizes the autocorrelation value in this manner, the overall tendency of the change in the autocorrelation value can be easily compared even if the autocorrelation value differs depending on the waveform of the heart rate.

The image generation unit 233 generates, on the basis of the autocorrelation value input from the correlation value calculation unit 232, the autocorrelation image data which visualizes a relationship between (i) the autocorrelation value and (ii) the timing at which the magnitude of the lag and the heartbeat waves or the like corresponding to the time series data are measured. Specifically, by mapping pixel values corresponding to the autocorrelation values corresponding to combinations of timing and lag to a coordinate plane, in which the timing is assigned to a first axis and the lag is assigned to a second axis, the image generation unit 233 generates the autocorrelation image data in which the autocorrelation values are indicated for each of the coordinates corresponding to a combination of a timing and a lag.

The image generation unit 233 quantizes the autocorrelation values into a plurality of gradations (for example, 8 bits (256 gradations)), thereby converting the autocorrelation values into any of 256 pixel values (R, G, B values). The autocorrelation image data generated by the image generation unit 233 in this manner is visualized as an image having different colors according to the timings and the lags, such as a heat map.

It should be noted that the image generation unit 233 sets a width of the autocorrelation image data extending in the first axial direction to a width such that a region of the same pixel value in the autocorrelation image data corresponding to normal waveform data is approximately a straight line, for example. Since the image generation unit 233 generates the autocorrelation image data having such a width, the determination unit 235 or a doctor who visually recognizes the autocorrelation image data can easily distinguish between a case where the waveform data is normal and a case where the waveform data is abnormal. The image generation unit 233 inputs the generated autocorrelation image data to the image output unit 234.

The image output unit 234 outputs the autocorrelation image data input from the image generation unit 233. For example, the image output unit 234 displays the autocorrelation image data on a display, transmits the autocorrelation image data to a printer to print it, or transmits the autocorrelation image data to an external device via the communication unit 21. Also, the image output unit 234 outputs the autocorrelation image data to the determination unit 235.

The determination unit 235 determines whether or not arrhythmia or atrial fibrillation has occurred on the basis of a pattern of the autocorrelation image data, and outputs a determination result. The determination unit 235 determines whether or not arrhythmia or atrial fibrillation has occurred on the basis of a shape of a region including equivalent pixel values in the autocorrelation image data, for example. The determination unit 235 displays the determination result on the display, transmits the determination result to the printer to print it, or transmits the determination result to an external device via the communication unit 21.

Figure 5A:
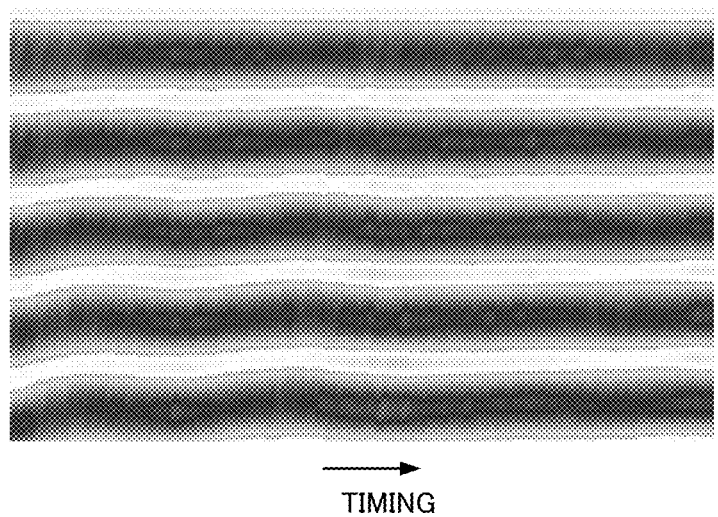
FIGS. 5A, 5B, and 5C each show an example of autocorrelation image data.
Figure 5B:
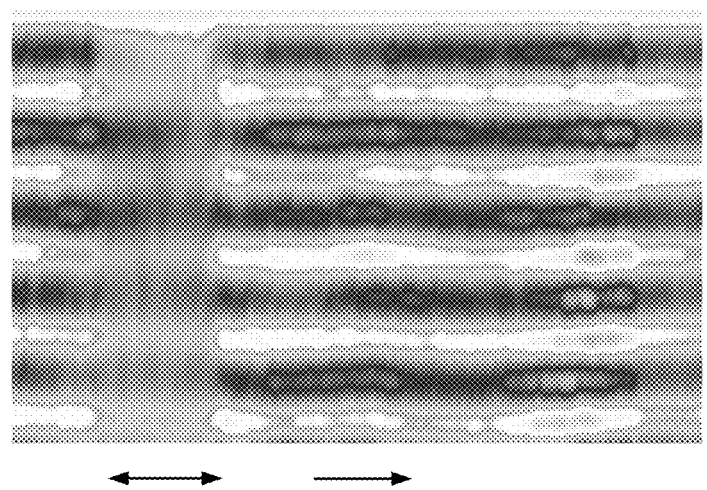
Figure 5C:
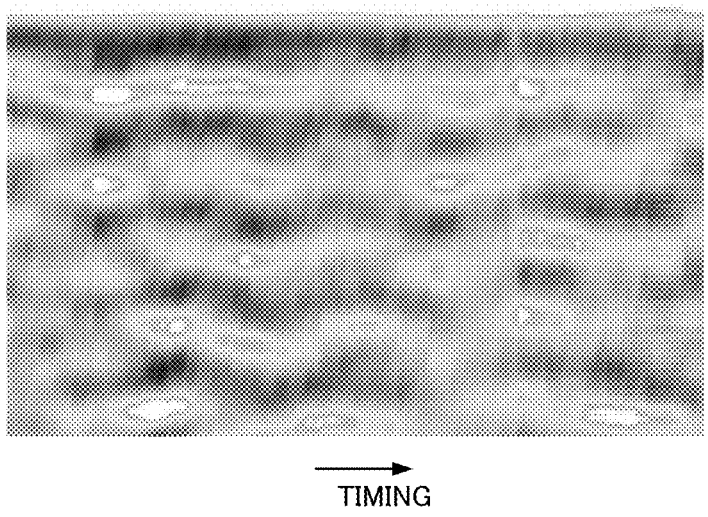

FIGS. 5A, 5B, and 5C each show an example of autocorrelation image data. In FIGS. 5A, 5B, and 5C, the horizontal axis (first axis) indicates the timing, and the vertical axis (second axis) indicates the lag. The upper left corresponds to an autocorrelation value when the timing and the lag are zero. The density (i.e., pixel value) of the images in FIGS. 5A, 5B, and 5C corresponds to the normalized autocorrelation value. In FIGS. 5A, 5B, and 5C, the closer the color is to white, the greater the autocorrelation value, and the closer the color is to black, the smaller the autocorrelation value.

FIG. 5A shows autocorrelation image data corresponding to normal heartbeat waves or the like in which sinus rhythm is present. FIG. 5B shows autocorrelation image data corresponding to heartbeat waves or the like in which arrhythmia is occurring. FIG. 5C shows autocorrelation image data corresponding to heartbeat waves or the like in which atrial fibrillation is occurring.

In the autocorrelation image data shown in FIG. 5A, the autocorrelation values are approximately constant for the same lag regardless of the timing. Further, as the lag changes, the autocorrelation value changes periodically at the same point in time.

In the autocorrelation image data shown in FIG. 5B, an amount of change in the autocorrelation value due to a change in the timing is greater than the amount of change in an example shown in FIG. 5A for the same lag. As a result, the number of places where the image corresponding to the same lag is interrupted is greater in FIG. 5B than in FIG. 5A. In particular, on both sides of the timing T0, the autocorrelation value greatly changes regardless of the value of the lag, and the determination unit 235 determines that there is an abnormality in the heartbeat waves or the like on the basis of the autocorrelation image data shown in FIG. 5B.

In the autocorrelation image data shown in FIG. 5C, a region of the same pixel value meanders as the timing (that is, in the horizontal-axis direction) changes. Such autocorrelation image data means intervals of pulses of the heartbeat waves or the like are fluctuating, and the determination unit 235 determines that atrial fibrillation is occurring on the basis of the autocorrelation image data shown in FIG. 5C.

The determination unit 235 determines whether or not arrhythmia or atrial fibrillation has occurred depending on whether or not a region corresponding to pixel values in a predetermined range (that is, a region in which a color is within a predetermined range) in the autocorrelation image data is continuous in the direction of the first axis. The predetermined range is a range in which a significant difference may occur in a shape of the region of the pixel values in the predetermined range between cases where the heart rate or the like is normal and where the heart rate or the like is abnormal.

As shown in FIG. 5A, the determination unit 235 determines that the heartbeat waves or the like are normal when the region of the pixel values in the predetermined range is (i) approximately linearly continuous along the horizontal axis in the autocorrelation image data and (ii) the region is not interrupted or meandering. On the other hand, when the pixel values corresponding to the same lag change over time, the determination unit 235 determines that the heartbeat waves or the like is abnormal because it is considered that the cycle of the pulses included in the heartbeat waves or the like is fluctuating. The determination unit 235 determines that the heartbeat waves or the like are abnormal when the region of the pixel values in the predetermined range is interrupted or meandering in the horizontal-axis direction in the autocorrelation image data, for example.

The determination unit 235 may determine whether or not arrhythmia or atrial fibrillation has occurred on the basis of the presence or absence of a region in which an amount of change in the plurality of pixel values corresponding to the plurality of pixels with respect to a distance between the plurality of pixels in the autocorrelation image data is equal to or greater than a threshold value. The determination unit 235 determines that arrhythmia or atrial fibrillation is occurring when there is more than a predetermined ratio of regions in which the amount of change in the pixel values of the plurality of pixels is equal to or greater than the maximum value of the amount of change assumed when the heartbeat waves or the like are normal, despite the distance between the plurality of pixels being small, as shown in FIG. 5B or FIG. 5C, for example.

In general, phenomena such as quivering in the baseline of the heartbeat waves or the like, absence of P waves, and fluctuations of RR intervals are observed during atrial fibrillation. Therefore, as shown in FIG. 5C, the determination unit 235 may determine that atrial fibrillation is occurring when the region corresponding to the pixel values in the predetermined range in the autocorrelation image data is not continuous in the direction of the first axis, and a curve connecting a plurality of regions corresponding to the same pixel value meanders as the timing changes.

Figure 6:
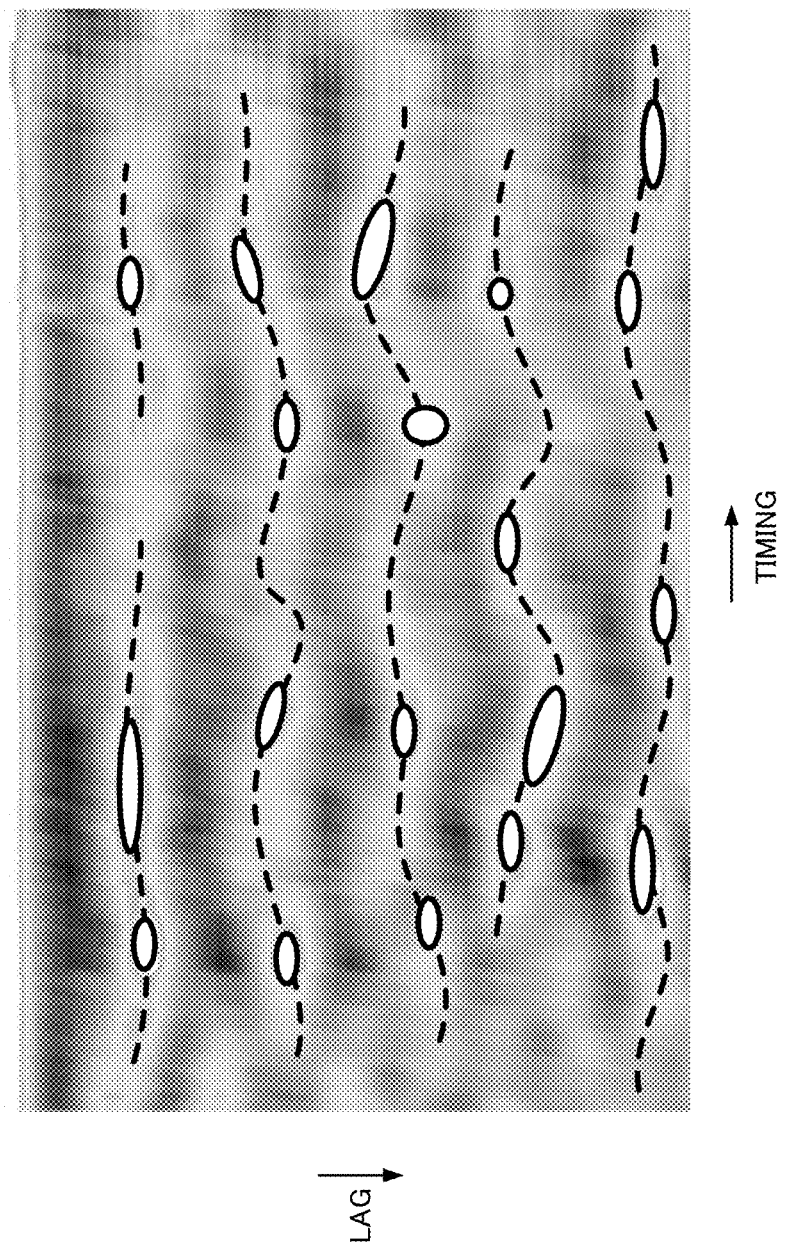
FIG. 6 shows autocorrelation image data corresponding to a state in which atrial fibrillation has occurred.

FIG. 6 shows autocorrelation image data corresponding to a state in which atrial fibrillation has occurred. FIG. 6 is an enlarged view of FIG. 5C. In FIG. 6, some portions of the plurality of regions corresponding to the same pixel value are indicated by the ellipses, and the curves connecting the plurality of regions corresponding to the same pixel value are indicated by the broken lines. In such a case, the determination unit 235 determines that atrial fibrillation is occurring. When the autocorrelation image data has a feature not applicable to any of FIG. 5A, 5B, or 5C, the determination unit 235 may output a result that the presence or absence of an abnormality cannot be determined.

The determination unit 235 may identify, among a plurality of pieces of reference image data generated in advance, reference image data most similar to the autocorrelation image data and determine that an abnormality corresponding to the identified reference image data is occurring. In this case, the storage unit 22 stores the plurality of pieces of reference image data associated with a plurality of abnormalities. The storage unit 22 stores a large number of pieces of autocorrelation image data based on the heartbeat waves or the like that are measured in the state in which atrial fibrillation has occurred, as reference image data of the state in which atrial fibrillation has occurred, for example.

The determination unit 235 compares (i) the autocorrelation image data input from the image output unit 234 with (ii) the plurality of pieces of reference image data stored in the storage unit 22. When reference image data of the state in which atrial fibrillation has occurred whose degree of similarity (e.g., correlation value) with the autocorrelation image data is equal to or greater than a threshold value is present in the storage unit 22, the determination unit 235 determines that the autocorrelation image data is the autocorrelation image data of a case where atrial fibrillation has occurred.

The storage unit 22 may store reference image data of a plurality of groups classified for each attribute of the heartbeat waves or the like. The attributes of the heartbeat waves or the like are elements that affect the waveform of the heart rate, such as the subject U's average heart rate, age, or body temperature. The storage unit 22 stores reference image data of a plurality of groups for each average value of the heart rate per minute, for example. In this case, the determination unit 235 compares (i) one or more pieces of reference image data belonging to a group corresponding to the heart rate identified from the heartbeat waves or the like corresponding to the autocorrelation image data, among the plurality of pieces of reference image data, with (ii) the autocorrelation image data. Because the determination unit 235 operates in this manner, determination accuracy can be improved and the time required for a determination can be reduced.

Using a machine learning model created by using (i) the autocorrelation image data based on the time series data acquired in the state where atrial fibrillation is occurring and (ii) the autocorrelation image data based on the time series data acquired in the state where atrial fibrillation is not occurring, as training data, the determination unit 235 may determine whether or not the autocorrelation image data is the autocorrelation image data of a case where atrial fibrillation has occurred. The machine learning model is a machine learning model that outputs a determination result of whether or not atrial fibrillation is occurring upon input of the autocorrelation image data. By inputting the autocorrelation image data generated by the image generation unit 233 to the machine learning model, the determination unit 235 determines whether or not atrial fibrillation has occurred.

In order to increase the accuracy of the determination result when the determination unit 235 makes determinations using the machine learning model, the determination unit 235 may use, from among a plurality of machine learning models classified for each attribute of the heartbeat waves or the like, a machine learning model corresponding to an attribute of the heartbeat waves or the like corresponding to the autocorrelation image data. For example, the determination unit 235 uses a machine learning model associated with an average value of the heart rate per minute of the heartbeat waves or the like corresponding to the autocorrelation image data to determine whether or not atrial fibrillation has occurred.

In order to achieve this, when a machine learning model in which the average value of the heart rate per minute corresponds to 60 seconds±5 seconds is created, for example, a plurality of machine learning models for heart rate are created using, as the training data, autocorrelation image data based on the heartbeat waves or the like in which the average value of the heart rate per minute falls within 60 seconds±5 seconds. Then, the determination unit 235 inputs the autocorrelation image data to the machine learning model corresponding to the heart rate identified from the heartbeat waves or the like corresponding to the autocorrelation image data among the plurality of machine learning models for heart rate. Because the determination unit 235 operates in this manner, the determination accuracy can be improved and the time required for the determination can be reduced.

Processing Flow of the Data Processing Apparatus 2

Figure 7:
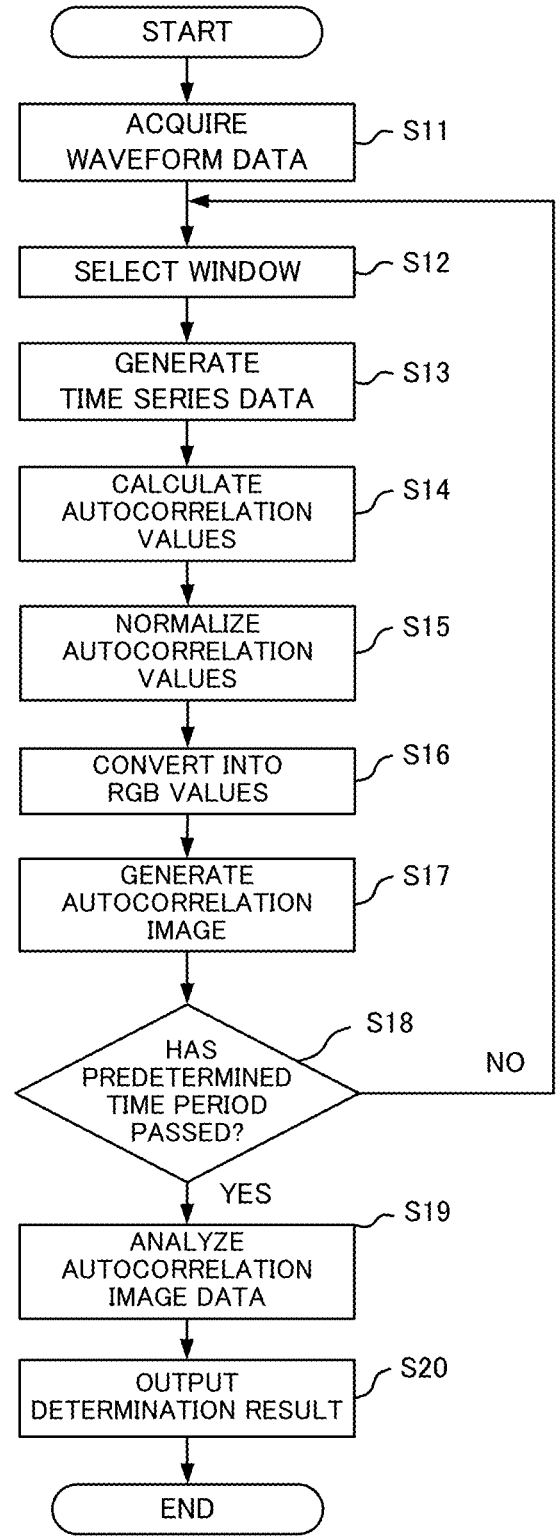
FIG. 7 is a flowchart showing a processing flow of the data processing apparatus.

FIG. 7 is a flowchart showing the processing flow of the data processing apparatus 2. The flowchart shown in FIG. 7 starts from a point in time when the heart rate meter 1 transmits waveform data.

First, the data acquisition unit 231 acquires the waveform data transmitted by the heart rate meter 1 (S11). The data acquisition unit 231 selects one window from among a plurality of windows having a predetermined window width included in the acquired waveform data (S12). The data acquisition unit 231 generates time series data to be used for calculating an autocorrelation value by cutting out a part of the waveform data corresponding to the selected window (S13).

Next, the correlation value calculation unit 232 calculates the autocorrelation values on the basis of the time series data generated by the data acquisition unit 231 (S14). The correlation value calculation unit 232 calculates an autocorrelation value for each of a plurality of different lags, and normalizes the autocorrelation values (S15). The correlation value calculation unit 232 converts the autocorrelation values after normalization into RGB values (S16). The correlation value calculation unit 232 associates the values of the lags with the RGB values and inputs them to the image generation unit 233. The image generation unit 233 generates, on the basis of the input RGB values, an autocorrelation image corresponding to the start timing of the window selected in step S12 (S17).

The correlation value calculation unit 232 determines whether or not the calculation of the autocorrelation values has been completed for the number of windows corresponding to a predetermined time period (for example, 1 minute) (S18), and proceeds to S19 if it is determined that the calculation of autocorrelation values has been completed over the predetermined time period (YES in S18). At this point in time, the autocorrelation image data as shown in FIGS. 5A, 5B, and 5C is generated, for example.

The correlation value calculation unit 232 returns the process to S12 if it is determined that the calculation of the autocorrelation values has not been completed over the predetermined time period (NO in S18).

When the autocorrelation image data is completed, the determination unit 235 analyzes the autocorrelation image data (S19), determines whether or not the autocorrelation image data indicates an abnormality, and outputs a determination result (S20).

It should be noted that, in the flowchart shown in FIG. 7, a case where the correlation value calculation unit 232 sequentially calculates autocorrelation values each time the data acquisition unit 231 acquires the waveform data, and the image generation unit 233 sequentially generates the autocorrelation image data was illustrated as an example. However, the correlation value calculation unit 232 and the image generation unit 233 do not need to perform these processes sequentially. The correlation value calculation unit 232 may calculate the autocorrelation values after waveform data of a predetermined period (for example, 1 minute) are accumulated in the storage unit 22, and the image generation unit 233 may generate the autocorrelation image data after the autocorrelation values corresponding to the predetermined period are calculated.

Variation Example

In the above description, as shown in FIGS. 3A, 3B, 3C, and 3D, a case where the correlation value calculation unit 232 calculates the autocorrelation values of the plurality of pieces of time series data corresponding to the plurality of windows shifted by a time less than the length of one cycle of the heartbeat waves or the like was illustrated as an example. In other words, a partial region of each window overlapped a partial region of another window. However, the plurality of windows do not need to overlap each other.

Figure 8A:
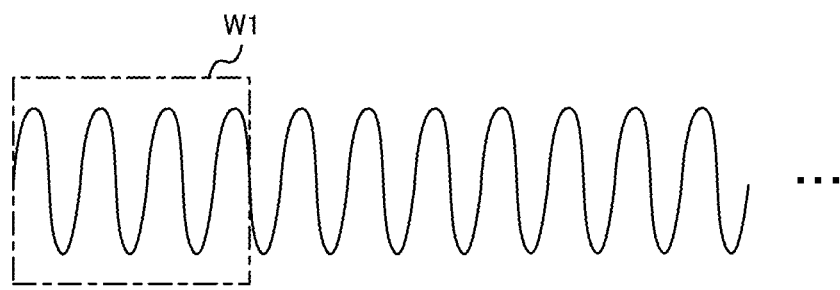
FIGS. 8A and 8B each show an example of a window according to a variation example.
Figure 8B:
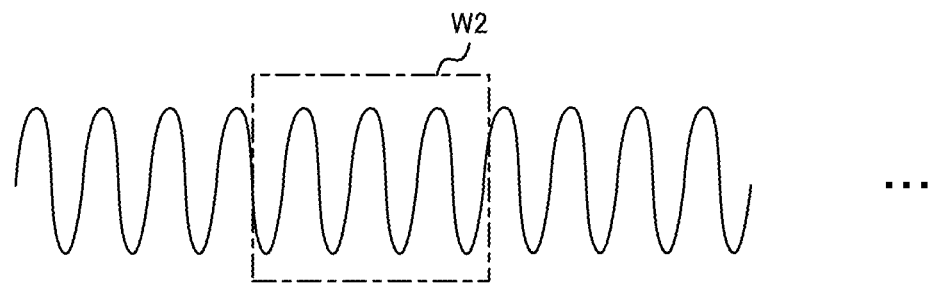

FIGS. 8A and 8B each show an example of a window according to a variation example. FIG. 8A shows a window W1 having a length equivalent to four cycles of pulse waves, and FIG. 8B shows a window W2 having an end timing of the window W1 as a start timing. The correlation value calculation unit 232 may sequentially calculate the autocorrelation values of the time series data in these windows.

Effect of the Data Processing Apparatus 2

As described above, the data processing apparatus 2 includes the correlation value calculation unit 232 that calculates, for each of the plurality of lags, the autocorrelation values of the plurality of pieces of time series data based on the waveform data of the heartbeat waves or the like, and the image generation unit 233 that generates the autocorrelation image data by mapping the pixel values corresponding to the plurality of autocorrelation values corresponding to the combinations of timing and lag. The determination unit 235 determines whether there is an abnormality in the heartbeat waves or the like on the basis of characteristics of the autocorrelation image data. Because the data processing apparatus 2 operates in this manner, it is possible to improve the detection accuracy of an abnormality in the heartbeat waves or the like.

Further, because the data processing apparatus 2 outputs the autocorrelation image data, a doctor who visually recognizes the autocorrelation image data can easily determine whether or not an abnormality is occurring in the heartbeat waves or the like. In addition, since the data processing apparatus 2 outputs the determination result by the determination unit 235 together with the autocorrelation image data, it is possible to reduce the probability that a doctor performing a diagnosis using autocorrelation image data will overlook a sign of atrial fibrillation.

The present disclosure is explained based on the exemplary embodiments. The technical scope of the present disclosure is not limited to the scope explained in the above embodiments and it is possible to make various changes and modifications within the scope of the disclosure. For example, all or part of the apparatus can be configured with any unit which is functionally or physically dispersed or integrated. Further, new exemplary embodiments generated by arbitrary combinations of them are included in the exemplary embodiments. Further, effects of the new exemplary embodiments brought by the combinations also have the effects of the original exemplary embodiments.

What is claimed is:

1. A data processing apparatus comprising:
a processor; and
a memory having instructions stored thereon that, when executed by the processor, cause the data processing apparatus to:
acquire waveform data corresponding to biological information correlated with a measured heart rate;
generate, based on the acquired waveform data, a plurality of pieces of time series data whose starting timings are different from each other, wherein the starting timings of each of the time series data are delayed from one another by a lag of a plurality of lags;
calculate autocorrelation values of the plurality of pieces of time series data for the lags of the plurality of lags;
generate autocorrelation image data by mapping pixel values corresponding to the autocorrelation values in a coordinate plane having a first axis and a second axis, wherein a timing corresponding to each autocorrelation value is assigned to the first axis and the lag corresponding to each autocorrelation value is assigned to the second axis;
select a machine learning model of a plurality of machine learning models based on the measured heart rate, wherein
the machine learning models of the plurality of machine learning models are each associated with an average heart rate, and a selected machine learning model is the machine learning model associated with an average heart rate corresponding to the measured heart rate, and
the machine learning models of the plurality of machine learning models are created by using (i) autocorrelation image data based on time series data acquired in a state where atrial fibrillation is occurring for an average heat rate associated with the machine learning model being created, and (ii) the autocorrelation image data based on the time series data acquired in a state where atrial fibrillation is not occurring for the average heart rate associated with the machine learning model being created, as training data;
input the autocorrelation image data to the selected machine learning model to determine whether or not arrhythmia or atrial fibrillation has occurred based on a pattern of the autocorrelation image data; and
output the autocorrelation image data.

2. The data processing apparatus according to claim 1, wherein the data processing apparatus is further caused to:
set a width of the autocorrelation image data extending in a direction of the first axis to a width that causes a region of a same pixel value in the autocorrelation image data corresponding to normal waveform data to be displayed as a straight line.

3. The data processing apparatus according to claim 1, wherein the determination of whether or not arrhythmia or atrial fibrillation has occurred is based on whether or not a region corresponding to pixel values in a predetermined range in the autocorrelation image data is continuous in a direction of the first axis.

4. The data processing apparatus according to claim 1, wherein the determination of whether or not arrhythmia or atrial fibrillation has occurred is based on a presence or absence of a region in which an amount of change in a plurality of pixel values corresponding to a plurality of pixels with respect to a distance between the plurality of pixels in the autocorrelation image data is equal to or greater than a threshold value.

5. The data processing apparatus according to claim 1, wherein the data processing apparatus determines atrial fibrillation has occurred in response to determining a curve which connects regions corresponding to pixel values in a predetermined range in the autocorrelation image data meanders as time changes.

6. The data processing apparatus according to claim 1, wherein the data processing apparatus is further caused to:
compare the autocorrelation image data to a plurality of pieces of reference image data associated with a plurality of abnormalities, wherein the plurality of pieces of reference image data are stored in a database;
identify reference image data of the plurality of pieces of reference data as being most similar to the autocorrelation image data based on a correlation value identifying a degree of similarity between the autocorrelation image data and the reference image data; and
determine an abnormality corresponding to the identified reference image data is occurring in response to the degree of similarity being greater than or equal to a preset threshold.

7. A data processing method that is executed by a computer, comprising:
acquiring waveform data corresponding to biological information correlated with a measured heart rate;
generate, based on the waveform data, a plurality of pieces of time series data whose starting timings are different from each other, wherein the starting timings of each of the time series data are delayed from one another by a lag of a plurality of lags;
calculating autocorrelation values of the plurality of pieces of time series data for the lags of the plurality of lags;
generating autocorrelation image data by mapping pixel values corresponding to the autocorrelation values in a coordinate plane having a first axis and a second axis, wherein a timing corresponding to each autocorrelation value is assigned to the first axis and the lag corresponding to each autocorrelation value is assigned to the second axis;

selecting a machine learning model of a plurality of machine learning models based on the measured heart rate, wherein the machine learning models of the plurality of machine learning models are each associated with an average heart rate, and a selected machine learning model is the machine learning model associated with an average heart rate corresponding to the measured heart rate, and the machine learning models of the plurality of machine learning models are created by using (i) autocorrelation image data based on time series data acquired in a state where atrial fibrillation is occurring for an average heat rate associated with the machine learning model being created, and (ii) the autocorrelation image data based on the time series data acquired in a state where atrial fibrillation is not occurring for the average heart rate associated with the machine learning model being created, as training data;

inputting the autocorrelation image data to the selected machine learning model to determine whether or not arrhythmia or atrial fibrillation has occurred based on a pattern of the autocorrelation image data; and outputting the autocorrelation image data.

8. A non-transitory storage medium storing a program that, when executed by a processor, causes a data processing apparatus to:

acquire waveform data corresponding to biological information correlated with a measured heart rate;

generate, based on the acquired waveform data, a plurality of pieces of time series data whose starting timings are different from each other, wherein the starting times of each of the time series data are delayed from one another by a lag of a plurality of lags;

calculate autocorrelation values of the plurality of pieces of time series data for the lags of the plurality of lags;

generate autocorrelation image data by mapping pixel values corresponding to the autocorrelation values in a coordinate plane having a first axis and a second axis, wherein a timing corresponding to each autocorrelation value is assigned to the first axis and the lag corresponding to each autocorrelation value is assigned to the second axis;

select a machine learning model of a plurality of machine learning models based on the measured heart rate, wherein the machine learning models of the plurality of machine learning models are each associated with an average heart rate, and a selected machine learning model is the machine learning model associated with an average heart rate corresponding to the measured heart rate, and the machine learning models of the plurality of machine learning models are created by using (i) autocorrelation image data based on time series data acquired in a state where atrial fibrillation is occurring for an average heat rate associated with the machine learning model being created, and (ii) the autocorrelation image data based on the time series data acquired in a state where atrial fibrillation is not occurring for the average heart rate associated with the machine learning model being created, as training data;

input the autocorrelation image data to the selected machine learning model to determine whether or not arrhythmia or atrial fibrillation has occurred based on a pattern of the autocorrelation image data; and output the autocorrelation image data.

\* \* \* \* \*